US00PP26223P2

(12) United States Plant Patent
Horvath

(10) Patent No.: US PP26,223 P2
(45) Date of Patent: Dec. 15, 2015

(54) ***GEUM* PLANT NAMED 'GIMLET'**

(50) Latin Name: ***Geum* hybrid**
Varietal Denomination: Gimlet

(71) Applicant: Brent Horvath, Fontana, WI (US)

(72) Inventor: Brent Horvath, Fontana, WI (US)

(73) Assignee: Brent Horvath, Fontana, IL (US)

( * ) Notice: Subject to any disclaimer, the term of this patent is extended or adjusted under 35 U.S.C. 154(b) by 117 days.

(21) Appl. No.: 13/987,903

(22) Filed: Sep. 16, 2013

(51) Int. Cl.
*A01H 5/00* (2006.01)

(52) U.S. Cl.
USPC ..... Plt./263.1

(58) Field of Classification Search
USPC ..... Plt./263.1
See application file for complete search history.

(56) References Cited

PUBLICATIONS

New Varieties 2012, p. 22.*

* cited by examiner

*Primary Examiner* — Keith Robinson

(57) ABSTRACT

A new, distinct *Geum* plant as shown and described, characterized by semi-double to single flowers that open yellow and fade to light yellow with creamy white tips.

1 Drawing Sheet

Latin name: *Geum* hybrid.
Cultivar name: 'Gimlet'.

BACKGROUND OF THE INVENTION

The present invention relates to a new and distinct hybrid of *Geum* plant named 'Gimlet' characterized by semi-double to single flowers that open yellow and fade to light yellow with creamy white tips. The new *Geum* was developed as a seedling as part of an on going breeding and selecting program, in Hebron, Ill. in 2008. The parents of the new plant are unknown. The selection of the new plant was due to its' semi-double to single flowers that open yellow and fade to light yellow with creamy white tips. The initial asexual propagation of the new plant was by division and took place at a nursery in Hebron, Ill. in 2009. Continued asexual propagation by division since that time has shown that the unique features of this new *Geum* plant are stable and reproduced true to type in successive generations.

SUMMARY OF THE INVENTION

In the following description, color references are made to The Royal Horticultural Society Colour Chart (2001). The new *Geum* plant named 'Gimlet' is characterized by semi-double to single flowers that open yellow RHS 4 A and fade to light yellow RHS 4 C with white tips colored close to RHS 155 C.

The new *Geum* plant can be compared to 'Banana Daiquiri' U.S. Plant Pat. No. 25,351 in that, flower colors are deeper yellow RHS 3 B while the new plant flower color is yellow RHS 4 A and fade to light yellow RHS 4 C with white tips colored close to RHS 155 C.

The new plant can also be compared to *Geum* 'Limoncello' not patented, which has bright yellow single flowers of 9 A while the new plant flower color is yellow RHS 4 A and fade to light yellow RHS 4 C with white tips colored close to RHS 155 C. Plants of *Geum* 'Limoncello' grow shorter to 30 cm tall while the new plant grows 40 cm tall at maturity. Plants of

*Geum*'Limoncello' have hairier darker green foliage RHS 147 A while the new plant has foliage color of RHS 137 A.

DESCRIPTION OF PHOTOGRAPHS

Figure 1:
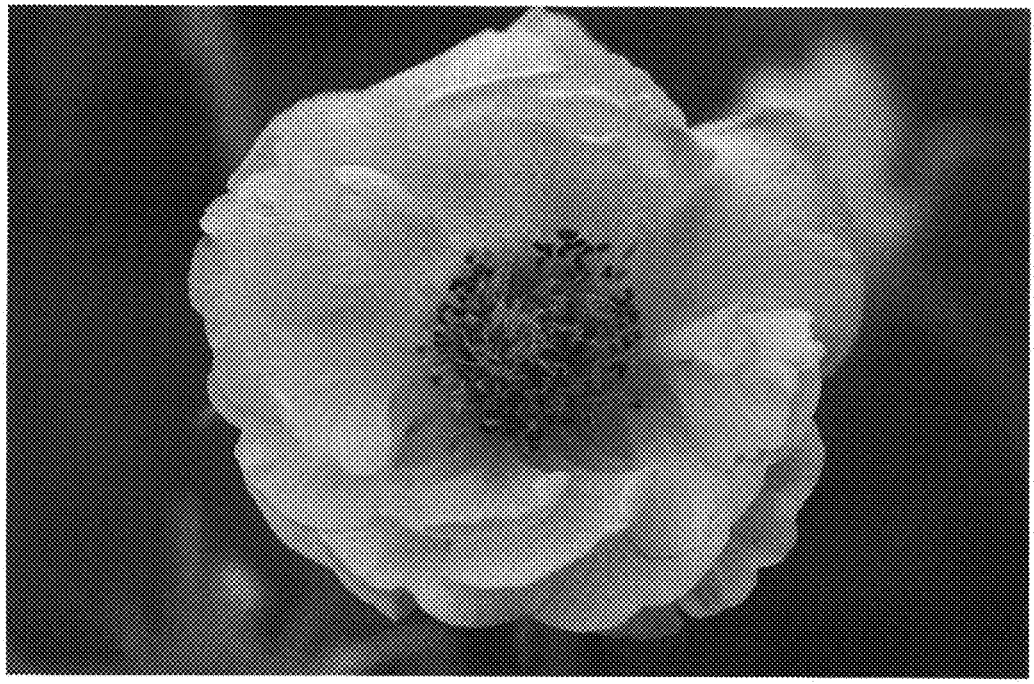

FIG. 1. Close up of the flower on an 8 month old plant in Hebron, Ill. USA.

Figure 2:
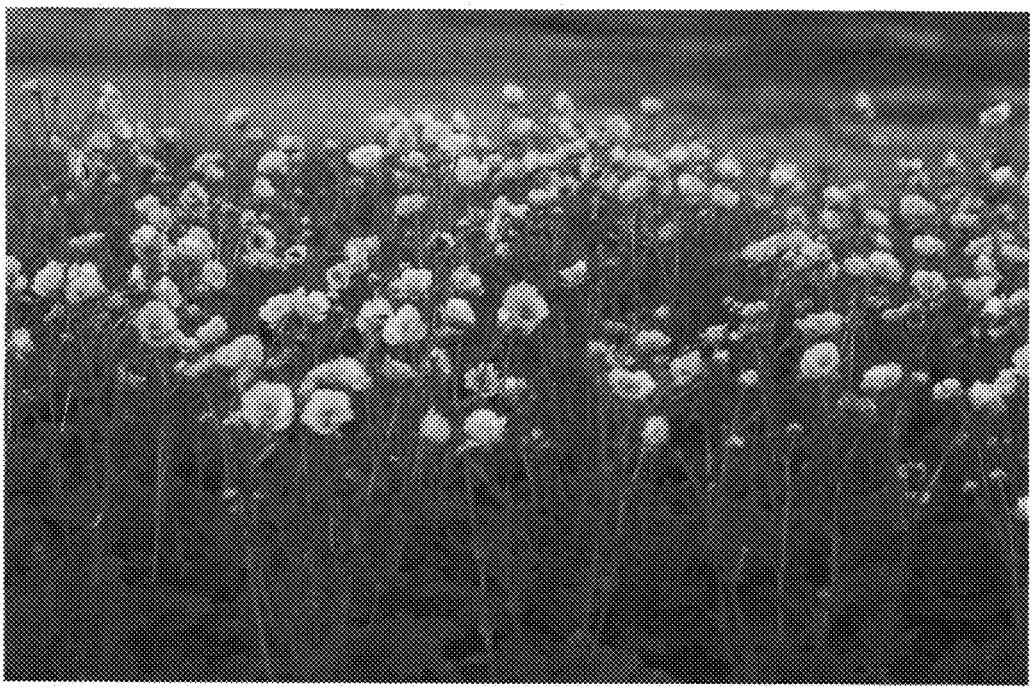

FIG. 2. One gallon, Blooming plants in May on an 8 month old plant in Hebron, Ill. USA.

DETAILED BOTANICAL DESCRIPTION

In the following description, color references are made to The Royal Horticultural Society Colour Chart (2001). Plants used for the description were grown in a 3 gallon container for two years at a nursery in Hebron, Ill. Measurements and numerical values represent averages of typical plants.

Botanical classification: *Geum* hybrid cultivar 'Gimlet'.

Parentage: Unknown.

Propagation: Vegetative division, vegetative unrooted cuttings taken in June in Hebron, Ill. USA, initiate roots in 4 weeks.

Roots: Fibrous, color close to 155 A.

Plant description: Overall habit of the new *Geum* is basal clumps, with medium vigor, upright green stems with semi-double to single flowers that open yellow RHS 4 A and fade to light yellow RHS 4 C with white tips colored close to RHS 155 C.

*Plant type*.—Herbaceous perennial.

*Plant height*.—40 cm.

*Plant width*.—50 cm.

*Stem*.—Diameter: 3 mm.

*Stem or basal branches*.—Length up to 40 cm, with the internode between basal foliage and first leaflet length being 10 cm and the second internode between the first leaflet and the second leaflet length being 5 cm and the third internode between the second and third leaflet length being 7 cm and the fourth internode between the third and fourth leaflet length being 4 cm.

*Stem coloration*.—146 D.

Foliage description:

*Type*.—Herbaceous.

*Arrangement*.—Basal alternate with typically two or three lateral leaflets per stem.

*Petiole*.—Up to 18 cm long, with a diameter of 3 mm, color is 146 D, pubescent.

*Terminal compound leaf length*.—Up to 20 cm.

*Terminal compound leaf width*.—8 cm.

*Terminal leaflet length*.—Typically 5 cm.

*Terminal leaflet width*.—Typically 8 cm.

*Terminal leaflet shape*.—Obovate with incised margins.

*Terminal and lateral leaf apex*.—Acute.

*Terminal and lateral leaf base*.—Cuneate.

*Terminal and lateral leaf margin*.—Incised.

*Texture*.—Terminal and lateral leaf, upper and lower surfaces: pubescent.

*Stipules*.—None observed.

*Venation pattern*.—Terminal and lateral leaf, upper and lower surfaces: pinnate.

*Venation color*.—Terminal and lateral leaf, upper surface is color 137 A and lower surface color is 146 D.

*Lateral leaflet number*.—2 or 3 per stem.

*Lateral leaflet length*.—2 cm.

*Lateral leaflet width*.—Up to 2 cm.

*Lateral leaflet shape*.—Obovate.

*Adaxial leaf description*.—Color is 137 A.

*Abaxial leaf description*.—Color 146 B.

Flower description:

*Flower type*.—Corymb.

*Flower color*.—Yellow RHS 4 A and fade to light yellow RHS 4 C with white tips colored close to RHS 155 C on top and close to 4 D on the bottom with white tips colored close to RHS 155 C.

*Flower size*.—Diameter: 40 mm across, depth 18 mm.

*Flower number*.—4-5 per stem, 85-145 per plant.

*Number flowering stems*.—20-30.

*Bloom period and duration*.—Beginning the first week of May into the first week of June in Hebron, Ill.

*Flower longevity and duration on the plant*.—Approximately 3 weeks.

*Flower longevity and duration cut*.—Approximately one week.

*Individual flower duration*.—Approximately 1 to 2 weeks with petals eventually drying to a tan color.

*Scent*.—None.

*Petal count*.—17.

*Petal shape*.—Spatulate.

*Petal arrangement*.—Rotate, overlapping, unfused.

*Petal longevity*.—Self cleaning.

*Petal diameter or width*.—15 mm across and petal length — 18 mm long.

*Petal apex*.—Retuse, base: attenuate, margin: entire.

*Petal texture*.—Upper and lower surfaces: smooth, glabrous.

*Petal color*.—Upper surface is color 4 A at the base fading into 4 C with white close to 155 C at the tips.

*Petal color*.—Lower surface color is close to 4 D at the base blending into white at the tips.

*Overall corymb size*.—Diameter and height — 13 cm across, 12 cm long

*Flower buds*.—Diameter: 15 mm across, depth: 12 mm, shape: ovoid, surface: slightly pubescent and color is close to 146 D.

*Sepal size*.—Length: up to 13 mm, diameter: 8 mm at base coming to a point.

*Sepal quantity*.—6, fused at the base.

*Sepal shape*.—Lanceolate, apex: acute, base: cuneate, margin: entire.

*Sepal texture*.—Upper and lower surfaces: Pubescent.

*Sepal color*.—Adaxial color 146 D. Abaxial color close to 146 D.

*Peduncle color*.—146 D.

*Peduncle texture*.—Pubescent.

*Peduncle size*.—Length: 23 mm, diameter: 3 mm.

*Pedicel size*.—Length: 10 cm, diameter: 1-2 mm and color 146 D.

*Pedicel texture*.—Pubescent.

*Reproductive organs*.—Stamen — quantity over 100, length 1 cm. Anther — quantity: over 100, length: 1 mm, diameter: close to 0.5 mm. Anther color — 14 A, Filament color — 21 A. Pollen — typically present, color: 12A. Stigma — number over 50, width less than 1 mm, color 21 A. Style — number: over 50, length: 5 mm, shape — linear, color — 21 A. Pistil — number: over 50, length: 6 mm, diameter — less than 1 mm. Pistil color — tips 9 A, base 151 B. Ovaries — number: over 50 per bloom average, color: is 151 B.

*Fruit*.—Number: over 50 per bloom average, color: is brown, 200 A, tear shaped, length — 9 mm, width — 2 mm.

*Seed*.—Length 9 mm, width 2 mm, color — 151 B, texture — pubescent.

*Hardiness*.—USDA zone 4 to 9.

Disease resistance: Resistance to diseases common to *Geum* has not been observed on plants grown under nursery conditions.

I claim:

1. A new, distinct *Geum* plant as shown and described, characterized by semi-double to single flowers that open yellow and fade to light yellow with creamy white tips.

* * * * *